(12) United States Patent
Otsubo et al.

(10) Patent No.: US 7,404,812 B2
(45) Date of Patent: Jul. 29, 2008

(54) DISPOSABLE WEARING ARTICLE WITH IMPROVED FASTENING ARRANGEMENT

(75) Inventors: Toshifumi Otsubo, Kagawa-ken (JP); Tomoko Sugita, Kagawa-ken (JP)

(73) Assignee: Uni-Charm Corporation, Shikokuchuo-shi (JP)

(*) Notice: Subject to any disclaimer, the term of this patent is extended or adjusted under 35 U.S.C. 154(b) by 157 days.

(21) Appl. No.: 10/920,350

(22) Filed: Aug. 18, 2004

(65) Prior Publication Data
US 2005/0043700 A1 Feb. 24, 2005

(30) Foreign Application Priority Data
Aug. 19, 2003 (JP) .............................. 2003-207944

(51) Int. Cl.
*A61F 13/15* (2006.01)
(52) U.S. Cl. ............. 604/391; 604/385.01; 604/385.03; 604/386; 604/387
(58) Field of Classification Search ............ 604/385.01, 604/385.03, 385.04, 386, 387, 389, 390, 604/393
See application file for complete search history.

(56) References Cited

U.S. PATENT DOCUMENTS

| | | | | |
|---|---|---|---|---|
| 4,834,742 | A * | 5/1989 | Wilson et al. ................ | 604/389 |
| 6,307,120 | B1 * | 10/2001 | Glaug ........................ | 604/383 |
| 2002/0045879 | A1 * | 4/2002 | Karami ...................... | 604/391 |
| 2002/0095131 | A1 * | 7/2002 | Olson ......................... | 604/391 |
| 2006/0036229 | A1 * | 2/2006 | Rohrl ......................... | 604/389 |

FOREIGN PATENT DOCUMENTS

| | | | |
|---|---|---|---|
| EP | 1 374 815 A2 | * | 1/2004 |
| JP | 1994-55623 | | 8/1994 |
| JP | 10-005276 | | 1/1998 |
| JP | 10005276 A | * | 1/1998 |
| JP | 10-155834 | | 6/1998 |
| JP | 10155834 A | * | 6/1998 |
| JP | 11-89881 | | 4/1999 |
| JP | 11089881 A | * | 4/1999 |

(Continued)

OTHER PUBLICATIONS

Machine generated translation of JP 10-155834 A from Industrial Property Digital Library; www.ipdl.inpit.go.jp/homepg_e.ipdl.*

*Primary Examiner*—Tatyana Zalukaeva
*Assistant Examiner*—Michael G Bogart
(74) *Attorney, Agent, or Firm*—Lowe Hauptman Ham & Ham LLP

(57) ABSTRACT

A disposable wearing article includes first and second engagement members attached to the outer surface of a front waist region along transversely opposite side edge portions thereof so as to be spaced from each other by a given dimension in a longitudinal direction and third engagement members attached to in the inner surface of a rear waist region along transversely opposite side edge portions thereof. The first engagement embers are laid on the respective side edge portions in longitudinally upper zones, the second engagement members are laid on the side edge portions in longitudinally lower zones, the third engagement members are laid on the side edge portions in longitudinally intermediate zones and hooks are respectively formed on the outer surface of the first and second engagement members and on the inner surface of the third engagement members.

16 Claims, 15 Drawing Sheets

FOREIGN PATENT DOCUMENTS

| | | | |
|---|---|---|---|
| JP | 2003-70833 A | * | 3/2003 |
| JP | 2003-144493 A | * | 5/2003 |
| JP | 2003-230587 A | * | 8/2003 |
| JP | 2003-84736 A | * | 10/2003 |
| JP | 2003-339750 A | * | 12/2003 |

* cited by examiner

DISPOSABLE WEARING ARTICLE WITH IMPROVED FASTENING ARRANGEMENT

RELATED APPLICATIONS

The present application is based on, and claims priority from, Japanese Application Serial Number2003-207944, filed Aug. 19, 2003, the disclosure of which is hereby incorporated by reference herein in its entirety.

BACKGROUND OF THE INVENTION

The present invention relates to a disposable wearing article used to absorb and then to retain bodily waste discharged thereon.

There has already been disclosed a disposable wearing article having front and rear waist regions, a crotch region extending between these two waist regions, and engagement members extending in a longitudinal direction and attached to transversely opposite side edge portions in the front and rear waist regions so that the side edge portions of the front waist region and the side edge portions of the rear waist region may be connected together by means of these engagement members (See Japanese Unexamined Utility Model Application Publication No. 1994-55623, herein after referred to as "Citation"). One of the engagement members is defined by hooks constituting the so-called mechanical fastener and attached to the outer surface of the rear waist region along the transversely opposite side edge portions thereof and the other of the engagement members is defined by loops constituting the mechanical fastener and attached to the inner surface of the front waist region along the transversely opposite side edge portions thereof.

Parent or care personnel may put this article disclosed in Citation on the wearer's body in a manner as follows: along the respective transversely opposite side edges portions of the front and rear waist regions, the inner surface of the rear waist region is placed upon the outer surface of the front waist region; the hooks and the loops are put in mutual engagement to connect the front and rear waist regions with each other whereupon a waist-hole and a pair of leg-holes are formed; then the wearer's legs are guided through the waist-hole, then through the leg-holes; and finally the article is drawn upward along the wearer's waist.

If the hooks formed on the outer surface of the side edge portions in the front waist region are engaged with the loops formed on the inner surface of the side edge portions of the rear waist region but more or less staggered in the transverse direction to put the article disclosed in Citation, the loops laid in the longitudinally upper and lower zones of the side edge portions in the rear waist region are exposed on the inner side of the article. The exposed loops laid in the longitudinally upper zone come in contact with the wearer's front waist and the exposed loops laid in the longitudinally lower zone come in contact with the wearer's legs. These exposed loops uncomfortably irritate the wearer's skin.

For disposal of this article after used and soiled with the wearer's body waste, the crotch region may be folded onto the outer surface of the front waist region and the hooks attached to the side edge portions of the front waist region maybe engaged with the outer surface of the crotch region to maintain the article in such folded state. However, the hooks must be opposed to the outer surface of the crotch region by folding the side edge portions of the front waist region onto the inner side of the article and correspondingly increased trouble is required to fasten the used article for disposal. In addition, the hooks and the outer surface of the crotch region are affected by a peeling force intending to peel them off from each other and the article may be unintentionally unfolded.

SUMMARY OF THE INVENTION

In view of the problem as has been described above, it is an object of the present invention to provide a disposable wearing article improved so that the wearer is free from any uncomfortable feeling during use of the article and, after used and soiled with the wearer's body waste, the article can be easily folded up for disposal.

A disposable wearing article having front and rear waist regions, a crotch region extending between these waist regions and paired engagement members respectively to inner surfaces of said front and rear waist region along transversely opposite side edges thereof so that said front and rear waist regions may be connected together by means of said engagement members.

The improvement according to the present invention is in that said engagement members comprise first and second engagement members attached to the outer surface of said front waist region along the transversely opposite side edge portions thereof so as to be spaced from one another in a longitudinal direction by a given dimension and third engagement members attached to the inner surface of said rear waist region along the transversely opposite side edge portions thereof wherein said first engagement members are laid on said transversely opposite side edge portion of the front Waist region in longitudinally upper zones, said second engagement members are laid on said transversely opposite side edge portions of the front waist region in longitudinally lower zones and said third engagement members are laid on said transversely opposite side edge portions of the rear waist region in longitudinally intermediate zones and wherein a fastening means is provided on the respective outer surfaces of said first and second engagement members and the respective inner surfaces of said third engagement members.

According to one preferred embodiment of the invention, said transversely opposite side edge portions of the rear waist region can be fastened to the outer surface of said crotch region at desired positions thereon.

According to another preferred embodiment of the invention, a length dimension of said third engagement members measured in the longitudinal direction substantially corresponds to or slightly larger than a dimension by which said first and second engagement members are spaced from one another in the longitudinal direction.

According to still another preferred embodiment of the invention, a length dimension of said third engagement members measured in the longitudinal direction is smaller than a length dimension of said first and second engagement members measured in the longitudinal direction.

According to further another preferred embodiment of the invention, a total length dimension of said first, second and third engagement members measured in the longitudinal direction when these engagement members are aligned one with another in the longitudinal direction substantially corresponds to a length dimension of said transversely opposite side edge portions in said front and rear waist regions measured in the longitudinal direction.

In the disposable wearing article according to the present invention, the third engagement members are not present in the longitudinally upper zone nor the lower zones on the respective side edge portions of the rear waist region. Therefore, even if the positions at which these side edge portions of the respective waist regions are connected together are staggered in the transverse direction, there is no possibility that the third engagement members might be exposed on the inner side in the longitudinally upper and lower zones on the side edge portions of the rear waist region If the longitudinally upper and lower zones on the side edge portions of the rear waist region come in contact with the wearer's front waist region and legs, it is not apprehended that these zones might uncomfortably irritate the wearer's skin because none of the hooks are present in these zones and comes in contact with the wearer's skin.

In this article also, after the article has been put on the wearer's body, the front and rear waist regions can be reconnected together by means of the first, second and third engagement members and thereby the waist size of the article can be adjusted in conformity of the waist size of the individual wearers. In this way, a fitness of the article around the wearer's waist can be adjusted so as to prevent the article from slipping down along the wearer's waist.

In the article according to one preferred embodiment, the used article can be maintained in its folded up state for disposal by fastening the side edge portions of the rear waist region to the outer surface of the crotch region at appropriate positions by means of the third engagement members. It is unnecessary for this article to fold the side edge portions of the rear waist region onto the inner side of the article and the used article can be easily folded up merely by, pressing the side edge portions against the crotch region. Of the article folded up in this manner, the side edge portions of the rear waist region as well as the outer surface of the crotch region are not affected by any peeling force and there is no anxiety that the article having been folded up in this manner might be unintentionally unfolded.

In the article implemented in the manner that the length dimension of the third engagement members measured in the longitudinal direction is substantially corresponds to or slightly larger than the dimension by which the first and second engagement members are spaced from one another in the longitudinal direction, each column defined by these first, third and second engagement members arranged in this order in the longitudinal direction as the article is put on the wearer's body includes no blank zone between the first and third engagement members as well as between the third and second engagement members. Thus the front and rear waist regions are reliably connected together along the side edge portions thereof.

In the article implemented in the manner that the length dimension of the third engagement members measured in the longitudinal direction is smaller than the length dimension of the first and second engagement members measured in the longitudinal direction, it is not apprehended that the third engagement members might come in contact with the wearer's skin.

In the article implemented in the manner that the total length dimension of the first, second and third engagement members measured in the longitudinal direction when these engagement members are arranged in the longitudinal direction substantially corresponds to the length dimension of the side edge portions in the front and rear waist regions, the front and rear waist regions can be reliably connected together along the side edge portions thereof substantially over the full range of the length dimension thereof measured in the longitudinal direction by engaging these engagement members with the inner surface of the rear waist region and with the outer surface of the front waist region.

DETAILED DESCRIPTION OF THE PREFERRED EMBODIMENTS

Details of a disposable wearing article according to the present invention will be more fully understood from the description given hereunder with reference to the accompanying drawings.

Figure 1:
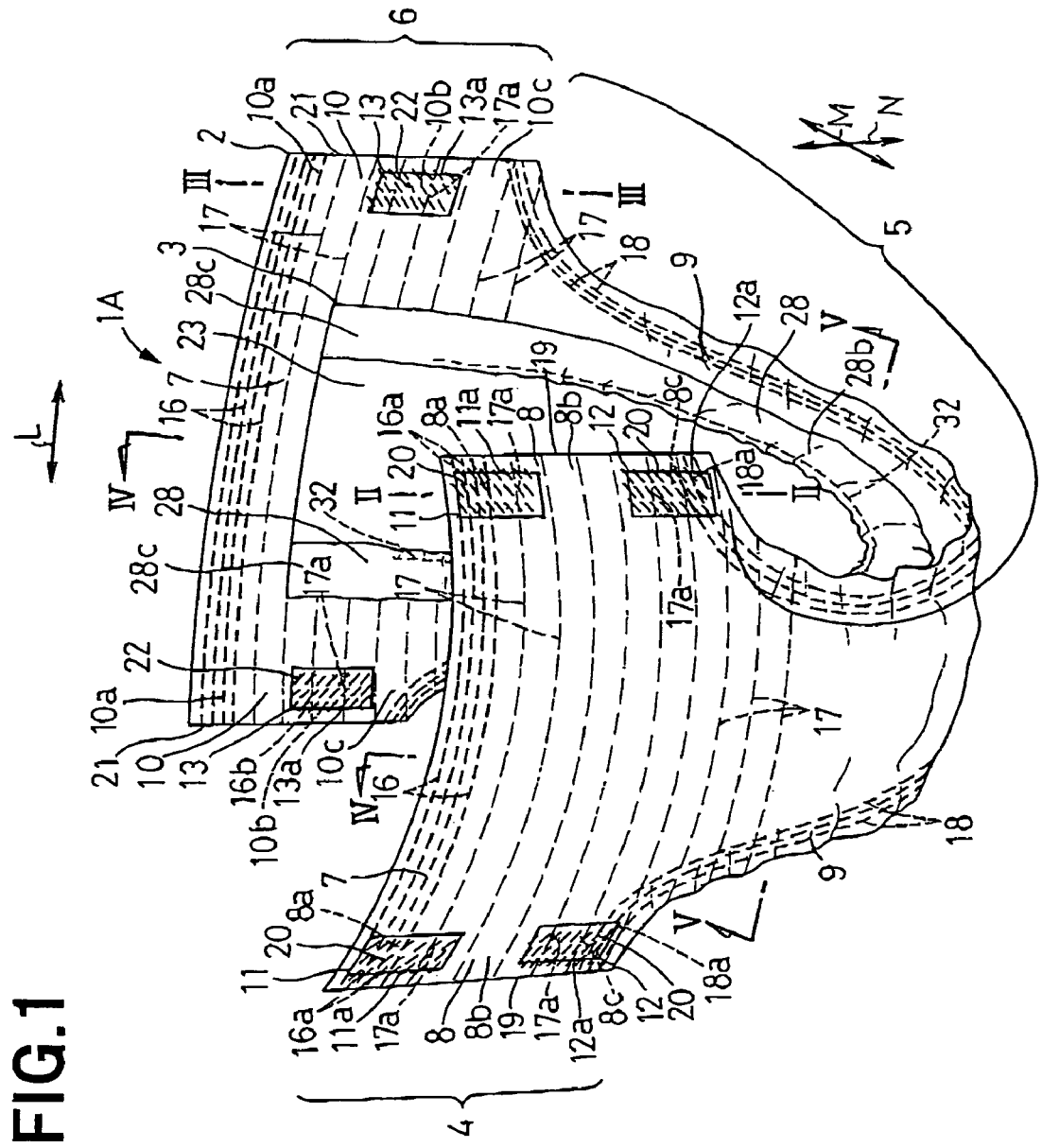
FIG. 1 is a perspective view showing a typical embodiment of the disposable wearing article.
Figure 2:
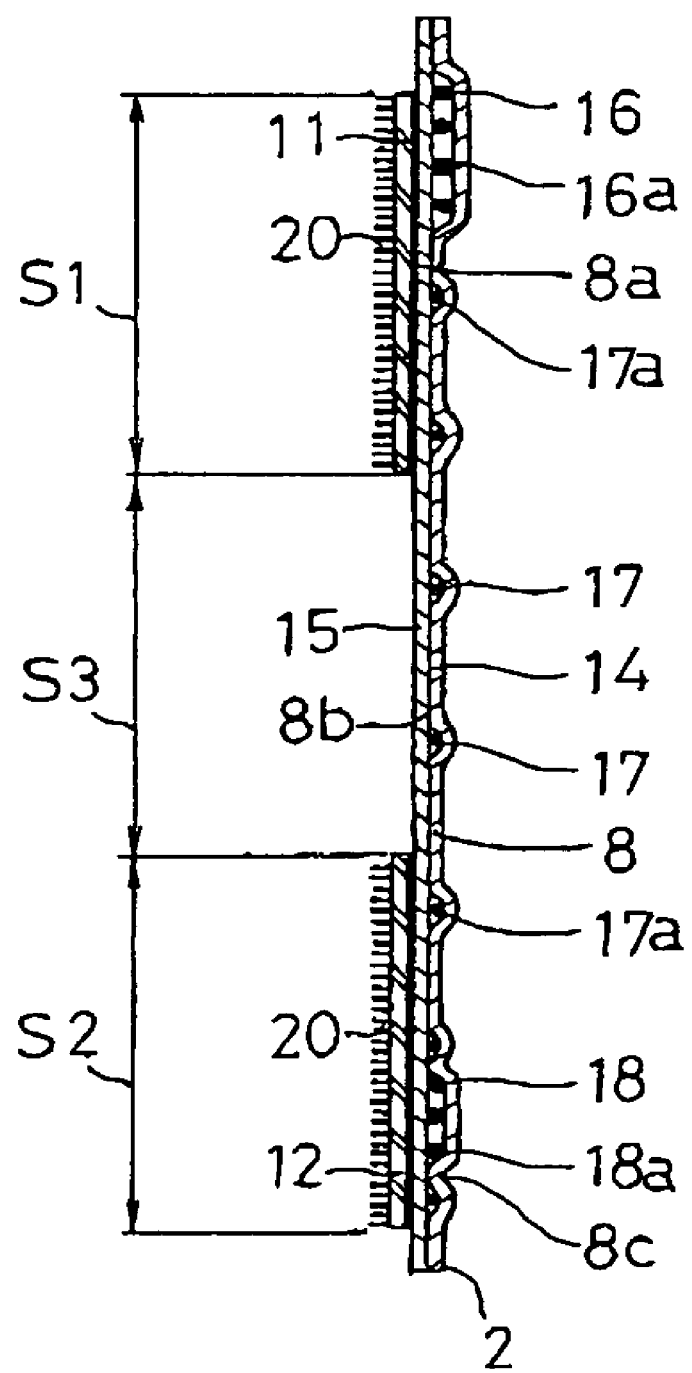
FIG. 2 is a sectional view taken along the line II-II in FIG. 1.
Figure 3:
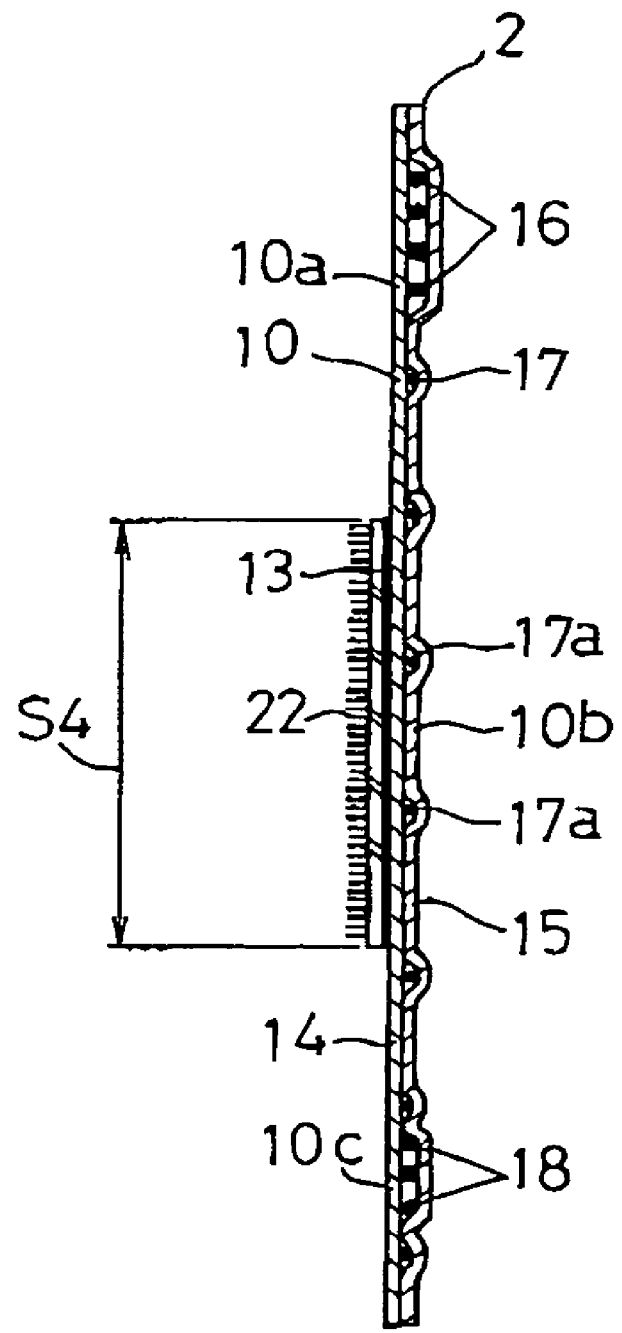
FIG. 3 is a sectional view taken along the line III-III in FIG. 1.
Figure 4:
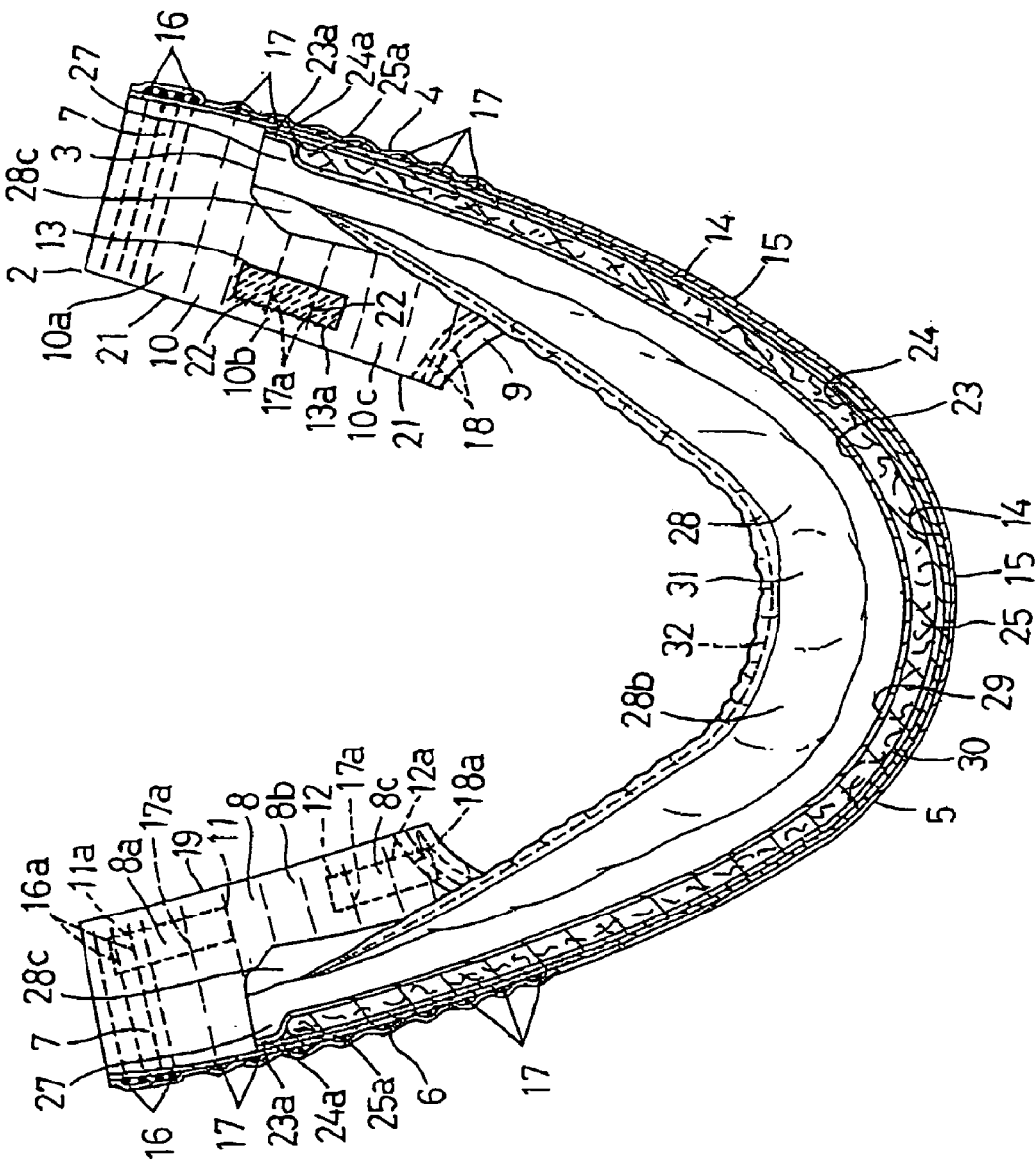
FIG. 4 is a sectional view taken along the line IV-IV in FIG. 1.

FIG. 1 is a perspective view showing a disposable wearing article 1A according to a typical embodiment of the invention, FIG. 2 is a sectional view taken along the line II-II in FIG. 1, FIG. 3 is a sectional view taken along the line III-III in FIG. 1 and FIG. 4 is a sectional view taken along the line IV-IV in FIG. 1. In FIG. 1, a transverse direction is indicated by an arrow L, a longitudinal direction is indicated by an arrow M and a thickness direction is indicated by an arrow N. As used herein, the term "inner surfaces" of an outer sheet 2, engagement members 11, 12, 13 and top- and backsheets 23, 24 refers to the surfaces thereof facing the wearer's skin and the term "outer surfaces" thereof refers to the surfaces thereof facing away from the wearer's skin.

The article 1A comprises a liquid-impervious outer sheet 2 defining an outer shape of the article 1A and a laminated panel 3 attached to the inner surface of the outer sheet 2. The article 1A defines, in a longitudinal direction, a front waist region 4, a rear waist region 6, a crotch region 5 extending between these waist regions 4, 6, longitudinally opposite end portions 7 extending across the front and rear waist regions 4, 6 in a transverse direction, and transversely opposite side edge portions 8, 9, 10 extending between the front rear waist regions 4, 6 in a longitudinal direction.

The side edge portions 8 of the front waist region 4 have substantially the same length dimension as a length dimension of the side edge portions 10 of the rear waist region 6. The side edge portions 8 of the front waist region 4 is provided first and second pairs of engagement members 11, 12, respectively, and the side edge portions 10 of the rear waist region 6 are provided with third pair of engagement members 13. The panel 3 presents a generally rectangular planar shape and extends between the front and rear waist regions 4, 6.

The outer sheet 2 defines the front and rear waist regions 4, 6, the crotch region 5, the longitudinally opposite end portions 7 and the transversely opposite side edge portions 8, 9, 10. The outer sheet 2 is formed from a composite nonwoven fabric composed of a pair of non-stretchable hydrophobic fibrous nonwoven fabric layers 14, 15 placed upon and bonded to each other. Mutually opposed surfaces of these nonwoven fabric layers 14, 15 are intermittently bonded to each other by means of adhesive (not shown). The outer sheet 2 curves inward along the side edge portions extending in the crotch region 5 so as to describe circular arcs which are convex in the transverse direction of the article 1A. Thus, the outer sheet 2 has a generally hourglass-like planar shape. A plurality of first and second waist-surrounding elastic members 16, 17 and a plurality of leg-surrounding elastic members 18 are contractibly attached to the outer sheet 2 so that the outer sheet 2 may be formed with a plurality of gathers as these elastic members 16, 17, 18 contract.

The first waist-surrounding elastic members 16 extend along the longitudinally opposite end portions 7 in the transverse direction. The first waist-surrounding elastic members 16 comprise a plurality of elastic strands arranged substantially at regular intervals in the longitudinal direction. The second waist-surrounding members 17 are laid between the first waist-surrounding elastic members 16 and the leg-surrounding elastic members 18 and extend across the front and rear waist regions 4, 6 in the transverse direction. The second waist-surrounding elastic members 17 comprise a plurality of elastic strands arranged substantially at regular intervals in the longitudinal direction. The leg-surrounding elastic members 18 comprise a plurality of elastic strands extending along the side edge portions 8, 9, 10 in the longitudinal direction from the crotch region 5 toward the front and rear waist regions 4, 6. These elastic members 16, 17, 18 are interposed between the nonwoven fabric layers 14, 15 constituting the outer sheet 2 and intermittently bonded to the mutual opposed surfaces of these nonwoven fabric layers 14, 15. Specifically, these elastic members 16, 17, 18 are bonded to these nonwoven fabric layers 14, 15 while these elastic members 16, 17, 18 are stretched at a predetermined ratio. The presence of these first and second waist-surrounding elastic members 16, 17 makes the respective side edge portions 8, 10 of the front and rear waist regions 4, 6 elastically stretchable in the transverse direction.

The first and second engagement members 11, 12 are provided in rectangular shapes which are relatively long in the longitudinal direction and arranged to be spaced from each other by a given dimension in the longitudinal direction. The first and second engagement members 11, 12 are attached to the outer surface of the front waist region 4 along the side edge portions 8 so as to be laid on longitudinally upper and lower portions 8a, 8c, respectively, on both sides of longitudinally intermediate portions 8b. More specifically, each of the first engagement members 11 has its inner surface permanently bonded to the outer surface of the outer sheet 2 (i.e., the nonwoven fabric 15) so as to be laid on the longitudinally upper zone 8a of the associated side edge portion 8 in the vicinity of its outermost edge 19. The first engagement members 11 are placed upon transversely opposite end portions 16a, 17a of the first and second waist-surrounding elastic members 16, 17. Each of the second engagement members 12 has its inner surface permanently bonded to the outer surface of the outer sheet 2 (i.e., the nonwoven fabric 15) so as to be laid on the longitudinally lower zone 8c of the associated side edge portion 8 in the vicinity of its outermost edge 19. The second engagement members 12 are placed upon the associated one of transversely opposite end portions 17a of the second elastic member 17 as well as upon the associated one of upper end portions 18a of the leg-surrounding elastic members 18. The first and second engagement members 11, 12 have respective outer side edges 11a, 12a laid inside the side edges 19 of the respective side edge portions 8 in order to protect the wearer's skin from uncomfortable irritation due to a direct contact of these outer side edges 1a, 12a with the wearer's skin. The first and second engagement members 11, 12 are formed over whole areas of the respective outer surfaces thereof with a plurality of hooks 20 constituting the mechanical fastener and these hooks 20 extend from the outer surfaces of these engagement members 11, 12 in the thickness direction of the article 1A.

The third engagement members 13 are provided in rectangular shapes which are relatively long in the longitudinal direction and attached to the inner surfaces of the respective side edge portions 10 in the rear waist region 6. Each of the third engagement members 13 has its outer surface permanently bonded to the inner surface of the outer sheet 2 (i.e., the nonwoven fabric 14) so as to be laid on a longitudinally intermediate zone 10b of the associated side edge portion 10 in the vicinity of its outermost edge 21. The third engagement members 13 are placed upon the transversely opposite end portions 17a of the second waist-surrounding elastic member 17. The third engagement members 13 have respective outer side edges 13a laid inside the side edges 21 of the respective side edge portions 10 in order to protect the wearer's skin from uncomfortable irritation due to a direct contact of these outer side edges 13a with the wearer's skin. The third engagement members 13 are formed over whole areas of the respective inner surfaces thereof with a plurality of hooks 22 constituting the mechanical fastener and these hooks 22 extend from the inner surfaces of the respective third engagement members 13 in the thickness direction of the article 1A.

Though not shown in Figs., it should be noted here that the hooks 20, 22 may be replaced by adhesive of the adhesive fastener known in the art.

A length dimension S4 of the third engagement member 13 measured in the longitudinal direction substantially corresponds to respective length dimensions S1, S2 of the first and second engagement members 11, 12 measured in the longitudinal direction and slightly smaller than a dimension S3 by which the first and second engagement members 11, 12 are spaced from each other in the longitudinal direction. A total length dimension S5 of the engagement members 11, 12, 13 arranged in the longitudinal direction generally corresponds to a length dimension S6 along which the side edge portions 8, 10 of the front and rear waist regions 4, 6 extend (See FIGS. 6 and 7)

Figure 5:
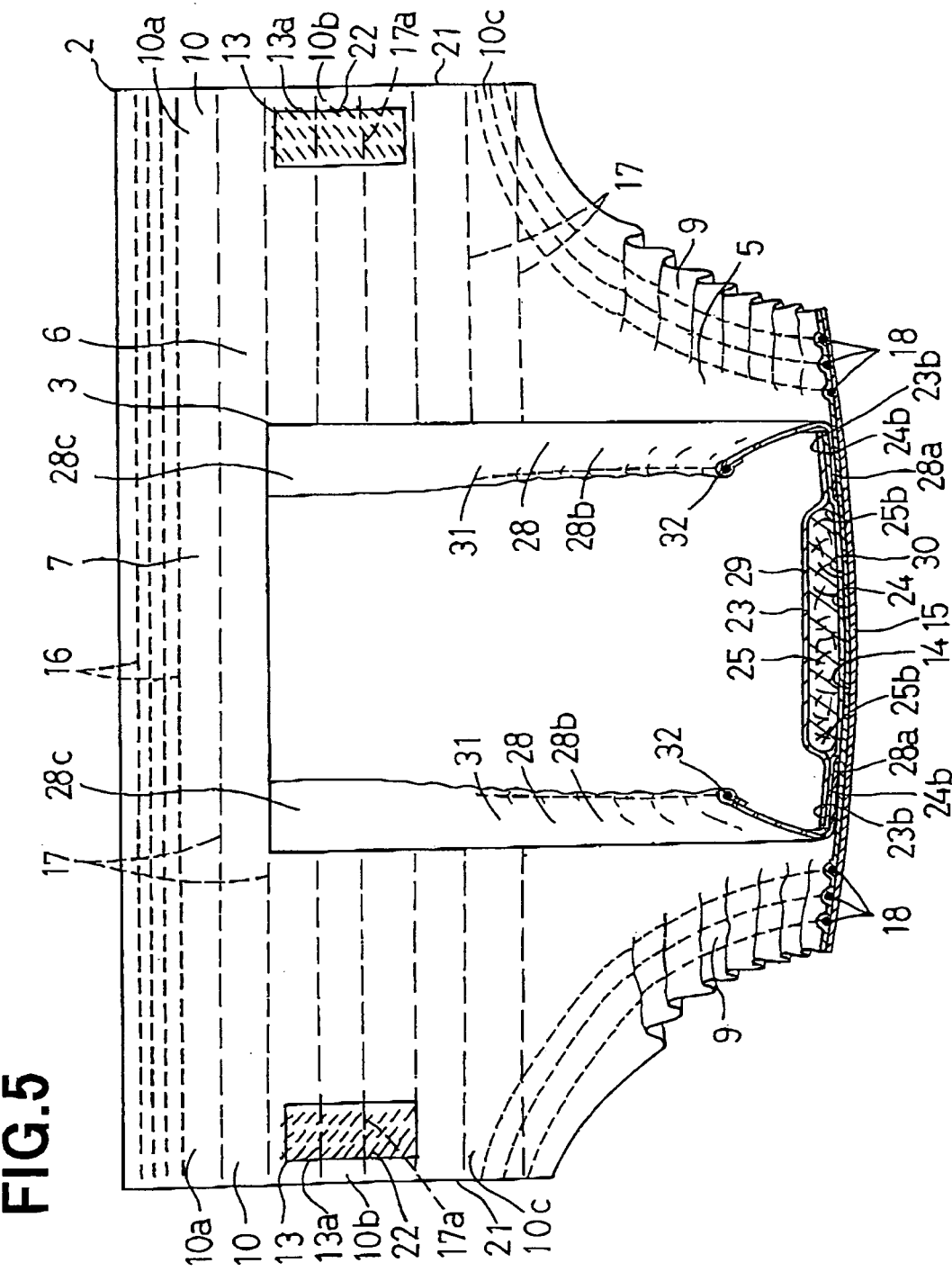
FIG. 5 is a sectional view taken along the line V-V in FIG. 1.

FIGS. 4 and 5 are sectional views taken along lines IV-IV and V-V, respectively, in FIG. 1.

The panel 3 comprises a liquid-pervious topsheet 23 facing the wearer's skin, a liquid-impervious backsheet 24 facing away from the wearer's skin and a liquid-absorbent core 25 interposed between these top- and backsheets, 23, 24. The panel 3 serves to absorb and to retain body waste discharged by the wearer of the article 1A. The panel 3 has longitudinally opposite ends 27 extending in the front and rear waist regions 4, 6 in the transverse direction and transversely opposite side edges 28 extending in the longitudinal direction between the front and rear waist regions 4, 6. In the panel 3, the outer surface of the backsheet 24 is permanently bonded to the inner surface of the outer sheet 2 (i.e., the nonwoven fabric layer 14) in intermittent or continuous manner. The transversely opposite side edges 27 of the panel 3 are respectively provided with a pair of liquid-resistant leak-barrier sheets 28 extending in the longitudinal direction between the front and rear waist regions 4, 6.

The topsheet 23 is formed from a hydrophilic fibrous nonwoven fabric 29 and the backsheet 24 is formed from a hydrophobic fibrous nonwoven fabric 30. The core 25 is permanently bonded to at least one of the top- and backsheets 23, 24. The core 25 comprises a mixture of particulate or fibrous super-absorbent polymer and fluff pulp or a mixture of particulate or fibrous super-absorbent polymer, fluff pulp and thermoplastic synthetic resin fiber, in any case, compressed to a given thickness. Preferably, the core 25 is entirely wrapped with liquid-pervious sheet such as tissue paper or hydrophilic-fibrous nonwoven fabric in order to prevent the core 23 from getting out of its initial shape and/or to prevent polymer from falling off. The polymer may be starch-based polymer, cellulose-based polymer or synthetic polymer.

The longitudinally opposite end portions 26 are formed from longitudinally opposite end portions 23a, 24a of the top- and backsheets 23, 24, respectively, extending outward in the longitudinal direction beyond the longitudinally opposite ends 25a of the core 25 In these end portions 26, the end portions 23a, 24a of the top- and backsheets 23, 24 are put flat and permanently bonded together. The transversely opposite side edge portions 27 are formed from transversely opposite side edge portions 23b, 24b of the top- and backsheets 23, 24, respectively, extending outward in the transverse direction beyond the transversely opposite side edges 25b of the core 25. In these side edge portions 27, the side edge portions 23b, 24b of the top- and backsheets 23, 24 are put flat and permanently bonded together.

The leak-barrier sheets 28 are formed from a hydrophobic fibrous nonwoven fabric 31. Each of these leak-barrier sheets 28 has a fixed lateral portion 28a extending in parallel to the associated side edge 27 of the panel 3 in the longitudinal direction, a movable portion 28b extending in parallel to the fixed lateral portion 28a in the longitudinal direction, and longitudinally opposite fixed end portions 28c of the movable portion 28b. The fixed lateral portion 28a is interposed between the outer sheet 2 and the backsheet 24 and permanently bonded to the inner surface of the outer sheet 2 (i.e., the nonwoven fabric layer 14) and the outer surface of the backsheet 24. A stretchable elastic member 32 extending in the longitudinal direction is contractibly attached to the movable portion 28b in the vicinity of its upper edge. The elastic member 32 is strand-like and permanently bonded to the movable portion 28b so that the elastic member 32 may be wrapped with a part of the movable portion 28b. The longitudinally opposite fixed end portions 28c lying on the respective end portions 26 of the panel 3 are collapsed inward in the transverse direction of the article 1A and permanently bonded in such state to the outer surface of the topsheet 23. The elastic member 32 contracts as the article A curves in the longitudinal direction with the panel 3 inside. In response to this, the movable portion 28b of the leak-barrier sheet 28 rises above the topsheet 23 and forms a barrier against body waste.

Figure 6:
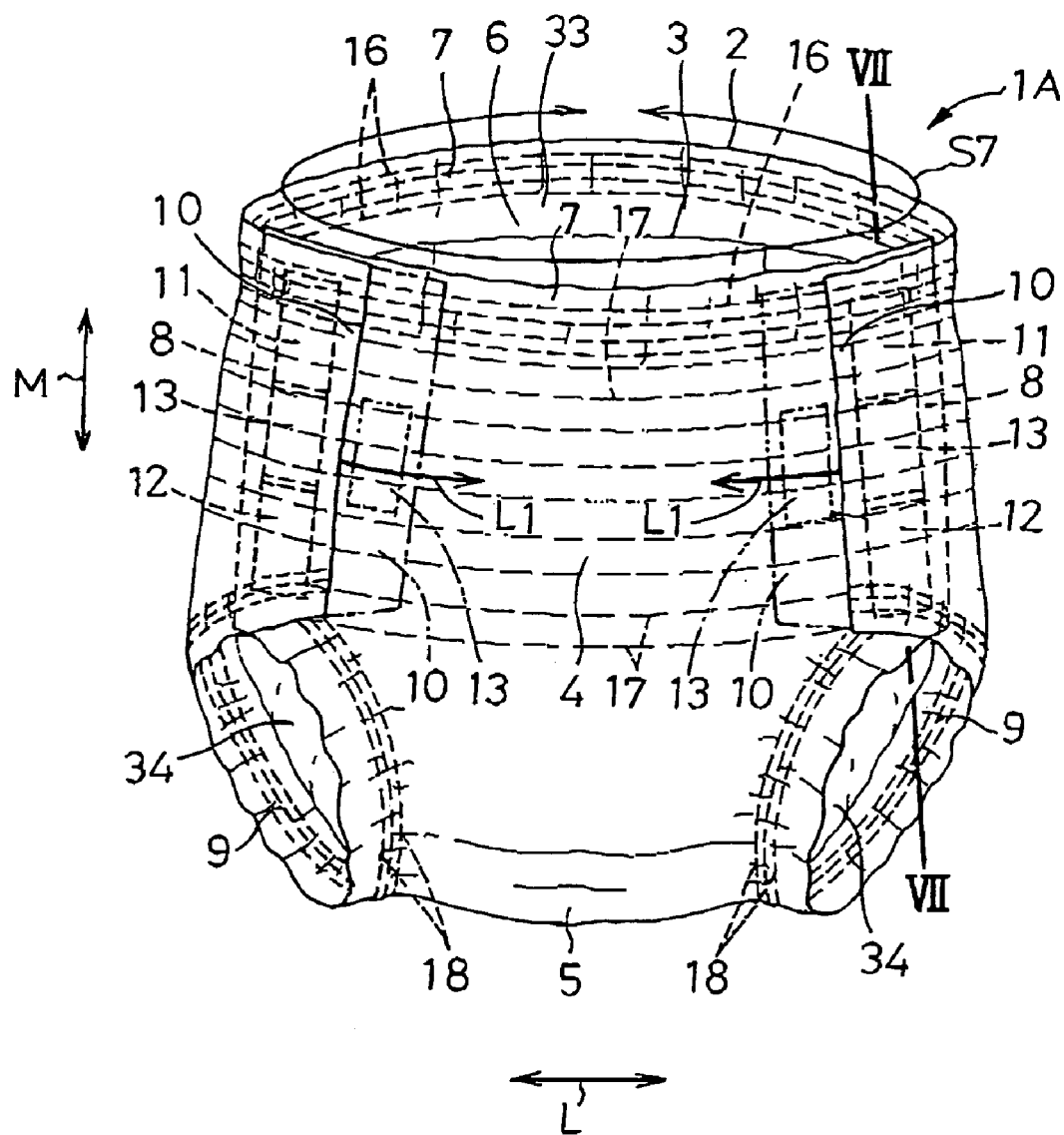
FIG. 6 is a perspective view showing the article of FIG. 1 as put on the wearer's body.
Figure 7:
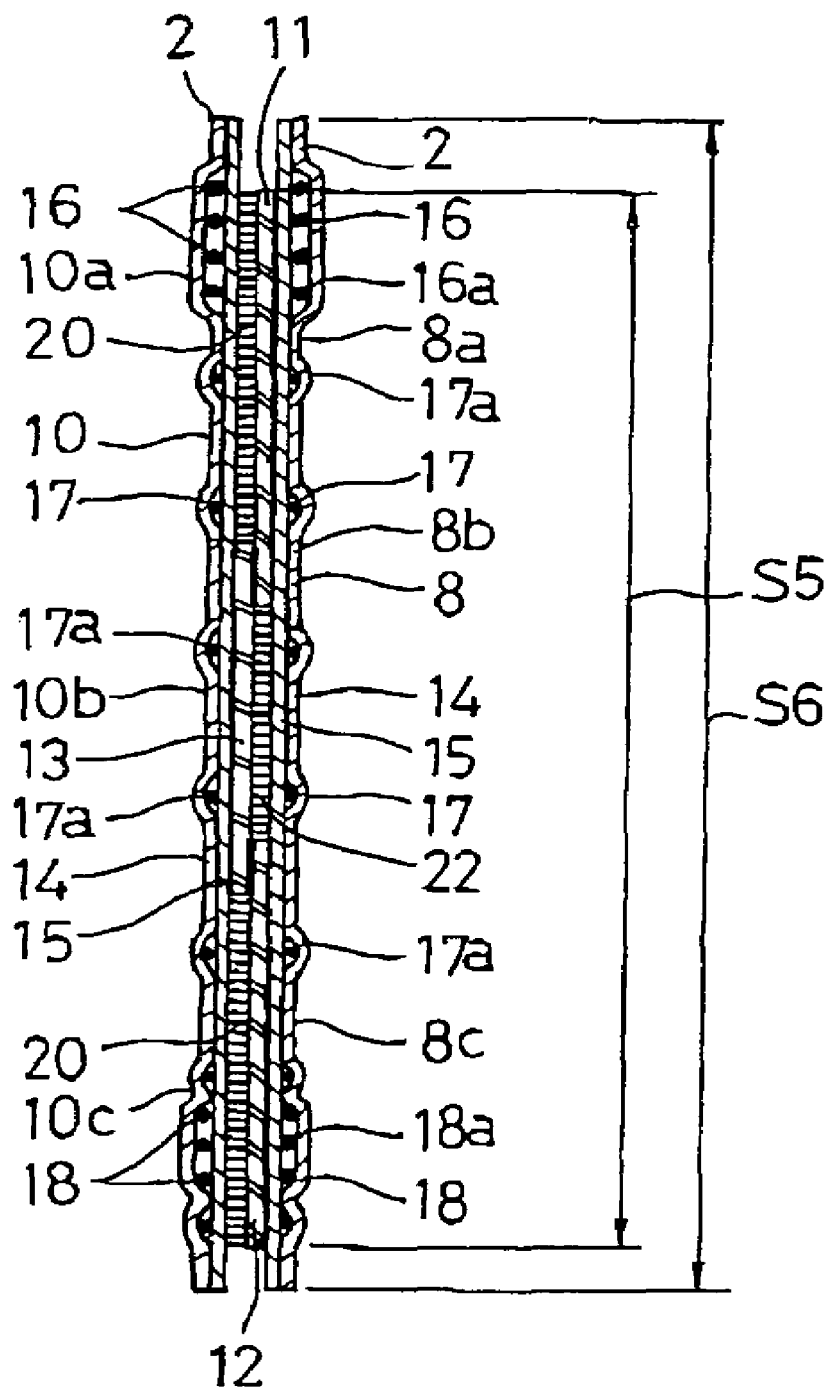
FIG. 7 is a sectional view taken along the line VII-VII in FIG. 6.
Figure 8:
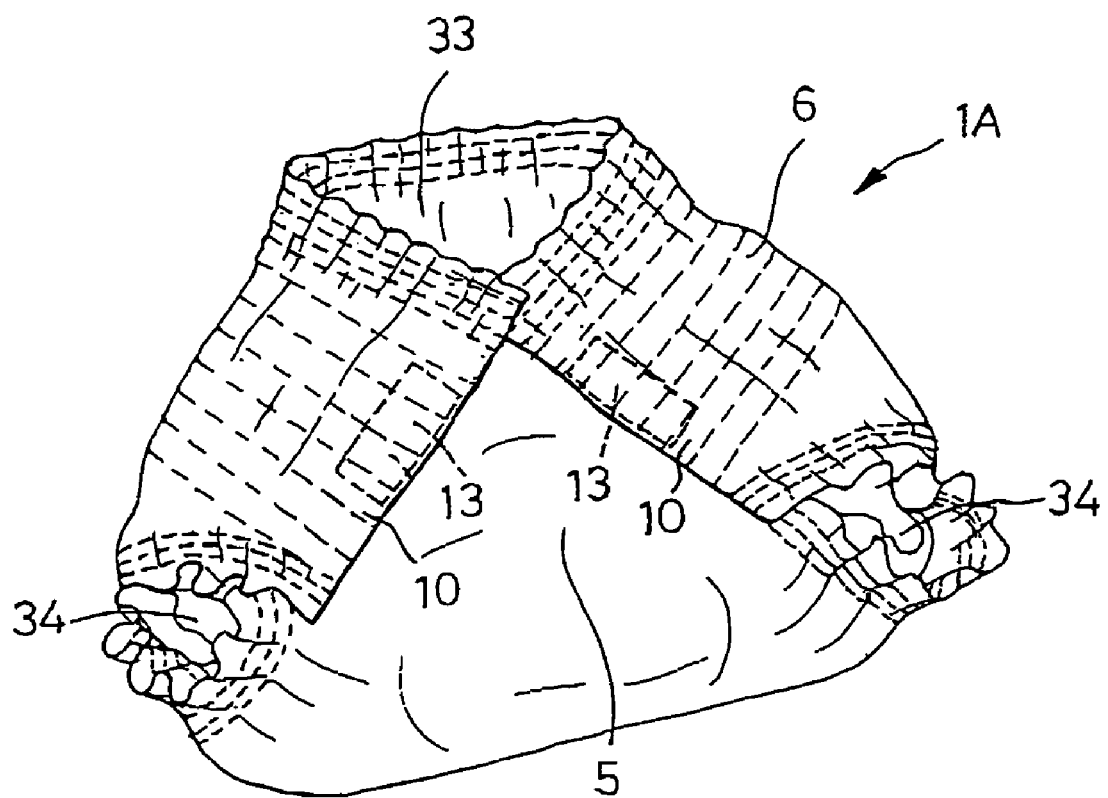
FIG. 8 is a perspective view showing the article of FIG. 1 as having been folded for disposal.

FIG. 6 is a perspective view showing the article 1A of FIG. 1 as put on the wearer's body, FIG. 7 is a sectional view taken along the line VII-VII in FIG. 6 and FIG. 8 is a perspective view showing the article 1A of FIG. 1 folded up after used in preparation for disposal. In FIG. 6, a transverse direction is indicated by an arrow L, a longitudinal direction is indicated by an arrow M and the side edge portions 10 of the rear waist region 6 having been moved toward a transversely middle zone of the front waist region 4 are indicated by chain double-dashed lines.

A sequence followed by parent or care personnel to put the article 1A on the wearer's body comprises steps of placing the inner surface of the rear waist region 6 upon the inner surface of the front waist region 4 along the side edge portions 10, 8 of the respective waist regions 4, 6 and pressing the side edge portions 10 of the rear waist region 6 against the side edge portions 8 of the front waist region 4. By pressing the side edge portions 10 against the side edge portions 8, the hooks 20 are caught by individual fibers of the nonwoven fabric layer 14 constituting the outer sheet 2 and thereby the first and second engagement members 11, 12 are engaged with the inner surface of the side edge portions 10 of the rear waist region 6. Simultaneously, the hooks 22 are caught by individual fibers of the nonwoven fabric layer 15 constituting the outer sheet 2 and thereby the third engagement member 13 is engaged with the outer surface of the side edge portions 8 of the front waist region 8. In this way, the front and rear waist regions 4, 6 are connected with each other along the side edge portions 8, 10 thereof. Thereupon, the article 1A is formed with a waist-hole 33 and a pair of leg-holes 34. After the front and rear waist regions 4, 6 have been connected with each other, parent or care personnel guides the wearer's legs through the waist-hole 33, then through the leg-holes 34 and draws the article 1A upward along the wearer's waist.

The third engagement members 13 are present neither in the longitudinally upper zone 10a nor in the longitudinally lower zone 10c of the respective side edge portions 10 of the rear waist region 6 and therefore there is no possibility that the third engagement members 13 might be exposed on the inner side of the article 1A even if the positions at which the side edge portions 8, 10 of the front and rear waist regions 4, 6 are connected together are shifted aside In the article 1A, even if the longitudinally upper and lower zones 10a, 10c of the side edge portions 10 contact with the wearer's front waist and legs, there is no anxiety that the wearer's skin might experience any uncomfortable irritation. This is for the reason that none of the hooks 22 are present in these zones 10a, 10c and merely the zones of the outer sheet 2 contact with the wearer's front waist and legs.

When the article 1A is put on the wearer's body and the first, second and third engagement members 11, 12, 13 are almost linearly aligned one with another in the longitudinal direction, each column defined by the first, second and third engagement members 11, 12, 13 includes none of blank zones (between the first and second engagement members 11, 13 linearly aligned with each other in the longitudinal direction as well as between the second and third engagement members 12, 13 linearly aligned with each other in the longitudinal direction) as will be apparently understood from FIGS. 6 and 7. Compared to the case in which the column defined by these engagement members 11, 12, 13 includes one or more blank zones, the side edge portions 8, 10 of the front and rear waist regions 4, 6 can be further more reliably connected together.

A total length dimension S5 of these engagement members 11, 12, 13 measured in the longitudinal direction substantially corresponds to a length dimension S6 of the side edge portions 8, 10 of the front and rear waist regions 4, 6. With such dimensioning, the side edge portions 8, 10 of the front and rear waist regions 4, 6 are engaged with one another over a generally full range of the length dimension S6 as the first, second and third engagement members 11, 12, 13 are engaged with the outer surface of the front waist region and the inner surface of the rear waist region 6. Thus these side edge portions 8, 10 of the front and rear waist regions 4, 6 can be reliably engaged with one another.

If it has been found that a fitness of the front and rear waist regions 4, 6 around the wearer's waist is insufficient after the article 1A was put on the wearer's body, parent or care personnel may disconnect the side edge portions 8, 10 of the front and rear waist regions 4, 6 one from another on the wearer's body and pull the side edge portions 10 of the rear waist region 6 toward the transversely intermediate zone of the front waist region 4 as indicated by the arrow L1, place the respective inner surfaces of the side edge portions 10 of the rear waist region 6 upon the outer surface of the front waist region 4 at desired positions and thereby connect again the front and rear waist regions 4, 6 by means of these first, second and third engagement members 11, 12, 13.

After the article 1A has been put on the wearer's body, the front and rear waist regions 4, 6 can be connected again with each other by means of the engagement members 11, 12, 13 as indicated by chain double-dashed lines. In this way, parent or care personnel may connect the side edge portions 10 of the rear waist region 6 with the side edge portions 8 of the front waist region 4 at the appropriate positions to ensure that a dimension S7 of the article 1A in the waist surrounding direction is adjusted in conformity with the individual wearer's waist size.

The first and second engagement members 11, 12 respectively lie on the transversely opposite end portions 16a, 17a of the first and second waist-surrounding elastic members 16, 17 and the longitudinally upper end portions 18a of the leg-surrounding elastic members 18 while the third engagement members lie on the transversely opposite end portions 17a of the second waist-surrounding elastic member 17. Such arrangement ensures that the elastic members 16, 17 are stretched in the transverse direction and the elastic members 18 are stretched in the longitudinal direction as the side edge portions 10 of the rear waist region 6 are pulled toward the transversely middle zone of the front waist region 4 and the inner surfaces of these side edge portions 10 are connected with the outer surface of the front waist region 4 at the appropriate positions. In this way, these elastic members 16, 17, 18 can be effectively utilized to tighten the article 1A around the wearer's waist and legs and thereby to maintain the article 1A in close contact with the wearer's waist and legs.

The used article 1A may be prepared for disposal, for example, in a manner as will be described hereunder. After the engagement members 11 have been disengaged from the front waist front and rear waist regions 4, 6 have disconnected from each other and left off from the wearer's body, parent or care personnel may fold the crotch region 5 onto the outer surface of the front waist region 4, then draw the side edge portions 10 of the rear waist region 6 toward a transversely intermediate zone of the crotch region 5 and press the side edge portions 10 of the rear waist region 6 against the outer surface of the crotch region 5. By pressing the side edge portions 10 against the crotch region 5, the hooks 20 are caught by the individual fibers of the nonwoven fabric layer 15 constituting the outer sheet 2 and thereby the side edge portions 10 of the rear waist region 8 can be fastened to the outer surface of the crotch region 5.

The used article 1A is maintained in its folded state by the third engagement members 13 as shown in FIG. 8 and therefore ready for disposal. More specifically, the waist-hole 33 as well as the leg-holes 34 of the used article 1A are maintained in closed state and therefore it is not apprehended that body waste or odor thereof might leak out from the article A through the waist-hole 33 and/or the leg-holes 34.

It is unnecessary for the article 1A to fold the side edge portions 10 of the rear waist region 6 toward the inner side of the article 1A for disposal, because the third engagement members 13 face the outer surface of the crotch region 5. Merely by pressing the side edge portions 10 against the outer surface of the crotch region 5, the article 1A can be effectively folded for disposal. In the article 1A folded in this manner, the side edge portions of the rear waist region 6 as well as the outer surface of the crotch region 5 are not affected by any peeling force intending to peel the third engagement members 13 off from the outer surface of the crotch region. In this way, there is no anxiety that the article 1A might be unintentionally unfolded.

Figure 9:
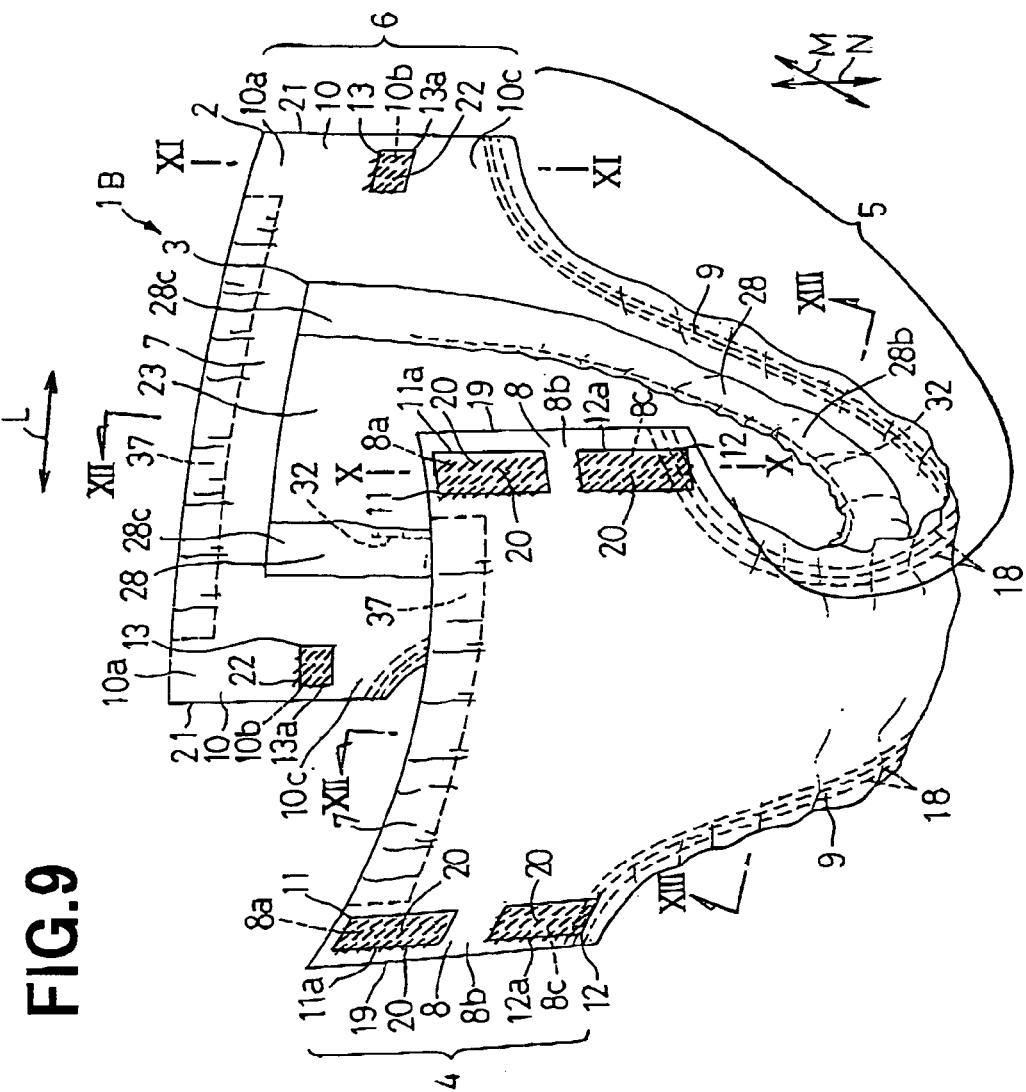
FIG. 9 is a perspective view showing another embodiment of the wearing article according to the invention.
Figure 10:
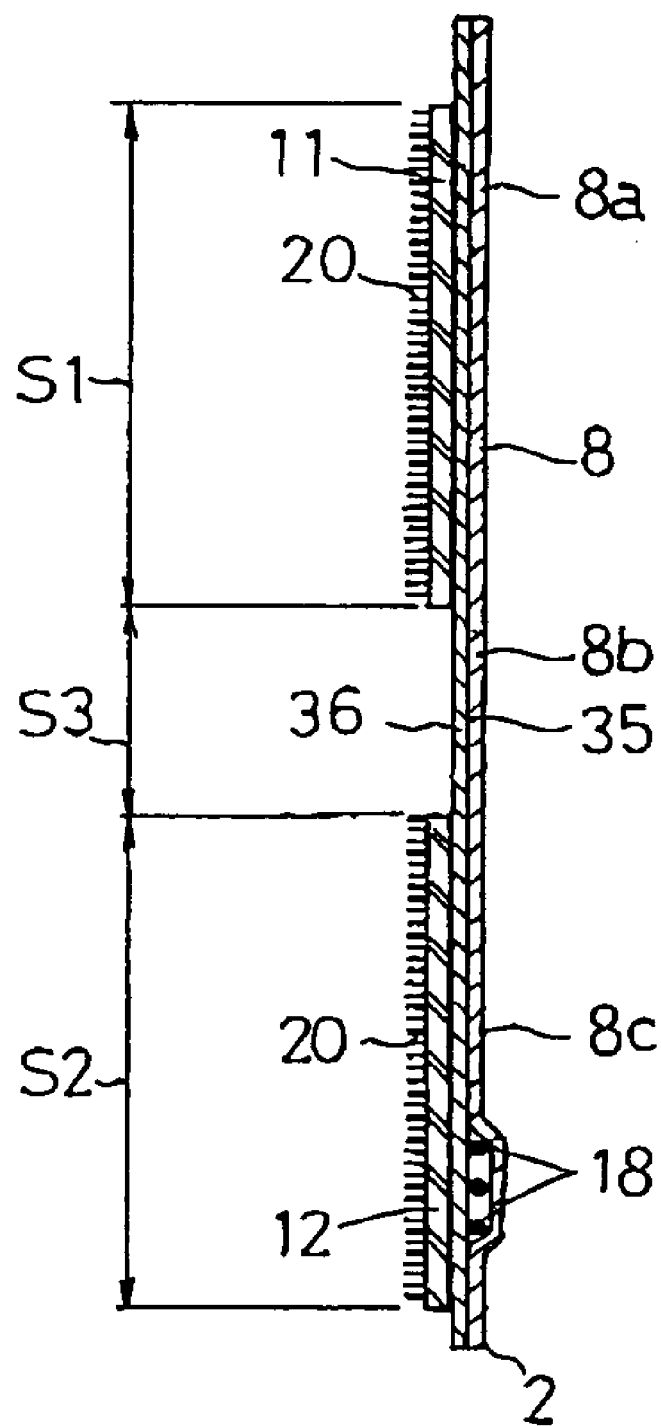
FIG. 10 is a sectional view taken along the line X-X in FIG. 9.
Figure 11:
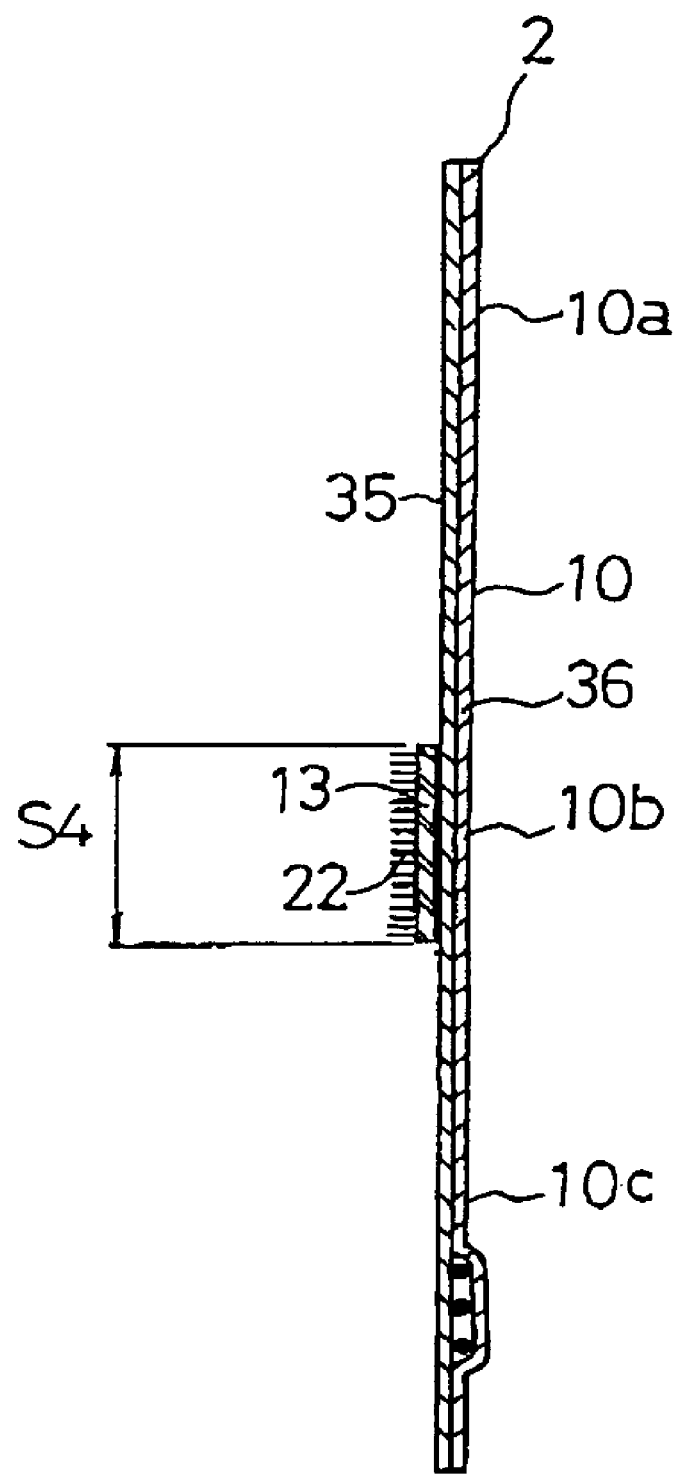
FIG. 11 is a sectional view taken along the line XI-XI in FIG. 9.

FIG. 9 is a partially cutaway perspective view showing a wearing article 1B according to another embodiment according to the invention, FIG. 10 is a sectional view taken along the line X-X in FIG. 9 and FIG. 11 is a sectional view taken along the line XI-XI in FIG. 9. In FIG. 9, a transverse direction is indicated by an arrow L, a longitudinal direction is indicated by an arrow M and a thickness direction is indicated by an arrow N.

The article 1B comprises a liquid-impervious outer sheet 2 and a laminated panel 3 attached to the inner surface of the outer sheet 2. The article 11 defines, in a longitudinal direction, a front waist region 4, a rear waist region 6 a crotch region 5 extending between these waist regions 4, 6, longitudinally opposite end portions 7 extending in a transverse direction, and transversely opposite side edge portions 8, 9, 10 extending in a longitudinal direction. The side edge portions 8 of the front waist region 4 have a substantially same length dimension as a length dimension of the side edge portions 10 of the rear waist region 6. First and second engagement members 11, 12 are attached to the side edge portions 8 of the front waist region 6 and third engagement members 13 are attached to the side edge portions 10 of the rear waist region 6. The panel 3 extends between the front and rear waist regions 4, 6.

The outer sheet 2 defines the front and rear waist regions 4, 6, the crotch region 5, the longitudinally opposite end portions 7 and the transversely opposite side edge portions 8, 9, 10. The outer sheet 2 is formed from a composite nonwoven fabric consisting of a pair of non-stretchable hydrophobic fibrous nonwoven fabric layers 35, 36 placed upon and bonded to each other. Mutually opposed surfaces of these nonwoven fabric layers 12, 13 are intermittently bonded to each other by means of adhesive (not shown). The outer sheet 2 curves inward along the side edge portions extending in the crotch region 5 so as to describe circular arcs which are convex in the transverse direction of the article 1B Thus, the outer sheet 2 has a generally hourglass-like planar shape. Waist-surrounding elastic members 37 and leg-surrounding elastic members 18 each comprising a plurality of elastic elements are contractibly attached to the outer sheet 2.

The waist-surrounding elastic members 37 are belt-like members and extend along the longitudinally opposite end portions 7 in the transverse direction. The leg-surrounding elastic members 18 comprise a plurality of elastic strands extending along the side edges 8, 9, 10 in the longitudinal direction These elastic members 18, 37 are interposed between the nonwoven fabric layers 35, 36 constituting the outer sheet 2 and intermittently bonded to the mutual opposed surfaces of these nonwoven fabric layers 35, 36. Specifically, these elastic members 35, 36 are bonded to these nonwoven fabric layers 18, 37 while these elastic members 18, 37 are stretched at a predetermined ratio. The respective side edge portions 8, 10 of the front and rear waist regions 4, 6 are elastically stretchable at least in the transverse direction of the longitudinal and transverse directions because the elastic members make the outer sheet 2 elastically stretchable.

The first and second engagement members 11, 12 are provided in rectangular shapes which are relatively long in the longitudinal direction and attached to the outer surface of the front waist region 4 along the side edge portions 8 so as to be spaced from each other by a given dimension in the longitudinal direction. Each of the first engagement members 11 has its inner surface permanently bonded to the outer surface (i.e., the nonwoven fabric 36) of the outer sheet 2 so as to be laid on a longitudinally upper zone 8a of the associated side edge portion 8 in the vicinity of its outermost edge 19. Each of the second engagement members 12 has its inner surface permanently bonded to the outer surface (i.e., the nonwoven fabric 36) of the outer sheet 2 so as to be laid on a longitudinally lower zone 8c of the associated side edge portion 8 in the vicinity of its outermost edge 19. The first and second engagement members 11, 12 have respective outer side edges 11a, 12a lying inside the side edges 19 of the respective side edge portions 8. The first and second engagement members 11, 12 are formed over whole areas of the respective outer surfaces thereof with a plurality of hooks 20 extending in the thickness direction of the article 1B.

The third engagement members 13 are provided in rectangular shapes which are relatively long in the longitudinal direction and attached to the inner surfaces of the respective side edge portions 10 in the rear- waist region 6. Each of the third engagement members 13 has its outer surface permanently bonded to the inner surface (i.e., the nonwoven fabric 35) of the outer sheet 2 so as to be laid on a longitudinally intermediate-zone 10b of the associated side edge portion 10 in the vicinity of its outermost edge 21. The third engagement members 13 have the outermost edges 13a lying inside the respective side edges 21 of the side edge portions 10. The third engagement members 13 are formed over whole areas of the respective inner surfaces thereof with a plurality of hooks 22 extending in the thickness direction of the article 1B. A length dimension S4 of the third engagement member 13 measured in the longitudinal direction is smaller than respective length dimensions S1, S2 of the first and second engagement members 11, 12 measured in the longitudinal direction and substantially corresponds to a dimension S3 by which the first and second engagement members 11, 12 are spaced from each other in the longitudinal direction. A total length dimension S5 of the engagement members 11, 12, 13 arranged in the longitudinal direction substantially corresponds to a length dimension S6 along which the side edge portions 8, 10 of the front and rear waist regions 4, 6 extend (See FIGS. 14 and 15).

Figure 12:
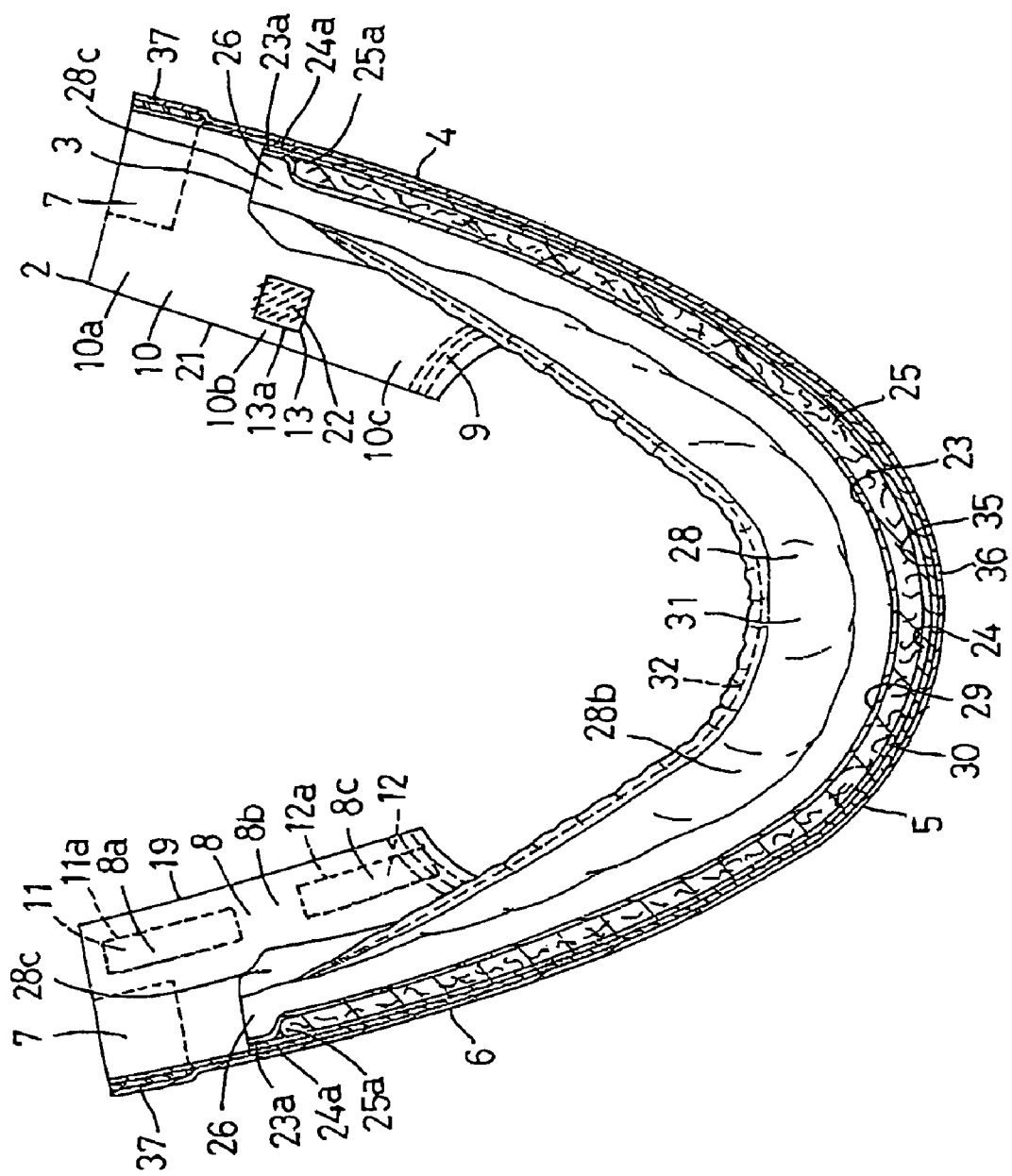
FIG. 12 is a sectional view taken along the line XII-XII in FIG. 9.
Figure 13:
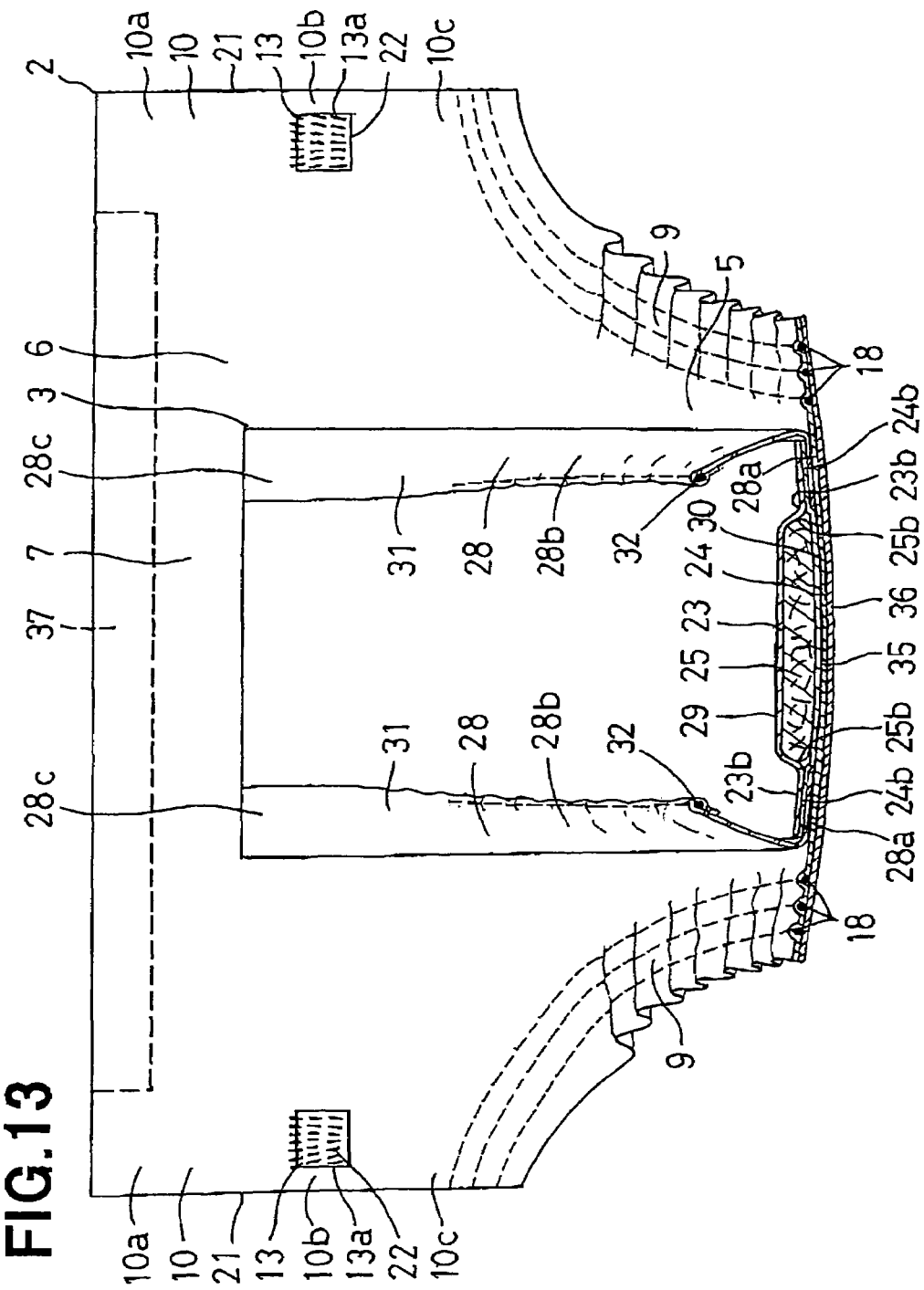
FIG. 13 is a sectional view taken along the line XIII-XIII in FIG. 9.

FIGS. 12 and 13 are sectional views taken along lines XII-XII and XIII-XIII, respectively, in FIG. 8.

The panel 3 comprises a liquid-pervious topsheet 23, a liquid-impervious backsheet 22 and a liquid-absorbent core 25 interposed between these top- and backsheets 23, 24 and bonded to at least one of these sheets 23, 24. The panel 3 serves to absorb and to retain body waste. The panel 3 has a substantially rectangular planar shape and extends between the front and rear waist regions 4, 6. The panel 3 has longitudinally opposite end portions 26 extending in the transverse direction and transversely opposite side edge portions 27 extending in the longitudinal direction. In the panel 3, the outer surface of the backsheet 24 is permanently bonded to the inner surface of the outer sheet 2 (i.e., the nonwoven fabric layer 35) in intermittent or continuous manner. The transversely opposite side edge portions 26 of the panel 3 are respectively provided with a pair of liquid-resistant leak-barrier sheets 28 extending in the longitudinal direction The top and backsheets 23, 24 are formed from a hydrophilic fibrous nonwoven fabric 29 and a hydrophobic fibrous nonwoven fabric 30 similar to those in the embodiment shown in FIG. 1. The core 25 is similar to that in the embodiment shown in FIG. 1.

The longitudinally opposite end portions 26 are formed from longitudinally opposite end portions 23a, 24a of the top- and backsheets 23, 24, respectively. In these end portions 26, the end portions 23a, 24a of the top- and backsheets 23, 24 are put flat and permanently bonded together. The transversely opposite side edge portions 27 are formed from transversely opposite side edge portions 23b, 24b of the top- and backsheets 23, 24, respectively, extending outward in the transverse direction beyond the transversely opposite side edges 25b of the core 25. In these side edge portions 27, the side edge portions 23b, 24b of the top- and backsheets 23, 24 are put flat and permanently bonded together.

The leak-barrier sheets 28 are formed from a hydrophobic fibrous nonwoven fabric 31 similar to that in the embodiment shown in FIG. 1. Each of these leak-barrier sheets 28 has a fixed lateral portion 28a extending in the longitudinal direction, a movable portion 28b extending in the longitudinal direction, and longitudinally opposite fixed end portions 28c of the movable portion 28b. The fixed lateral portion 28a is interposed between the outer sheet 2 and the backsheet 24 and permanently bonded to the inner surface of the outer sheet 2 (i.e., the nonwoven fabric layer 35) and the outer surface of the backsheet 24. A stretchable elastic member 32 extending in the longitudinal direction is contractibly attached to the movable portion 28b. The movable portion 28b rises above the topsheet 23 and forms a barrier against body waste as the elastic member 32 contracts. The longitudinally opposite fixed end portions 28c lying on the respective end portions 26 of the panel 3 are collapsed inward as viewed in the transverse direction of the article 1B and permanently bonded in such state to the outer surface of the topsheet 23.

Figure 14:
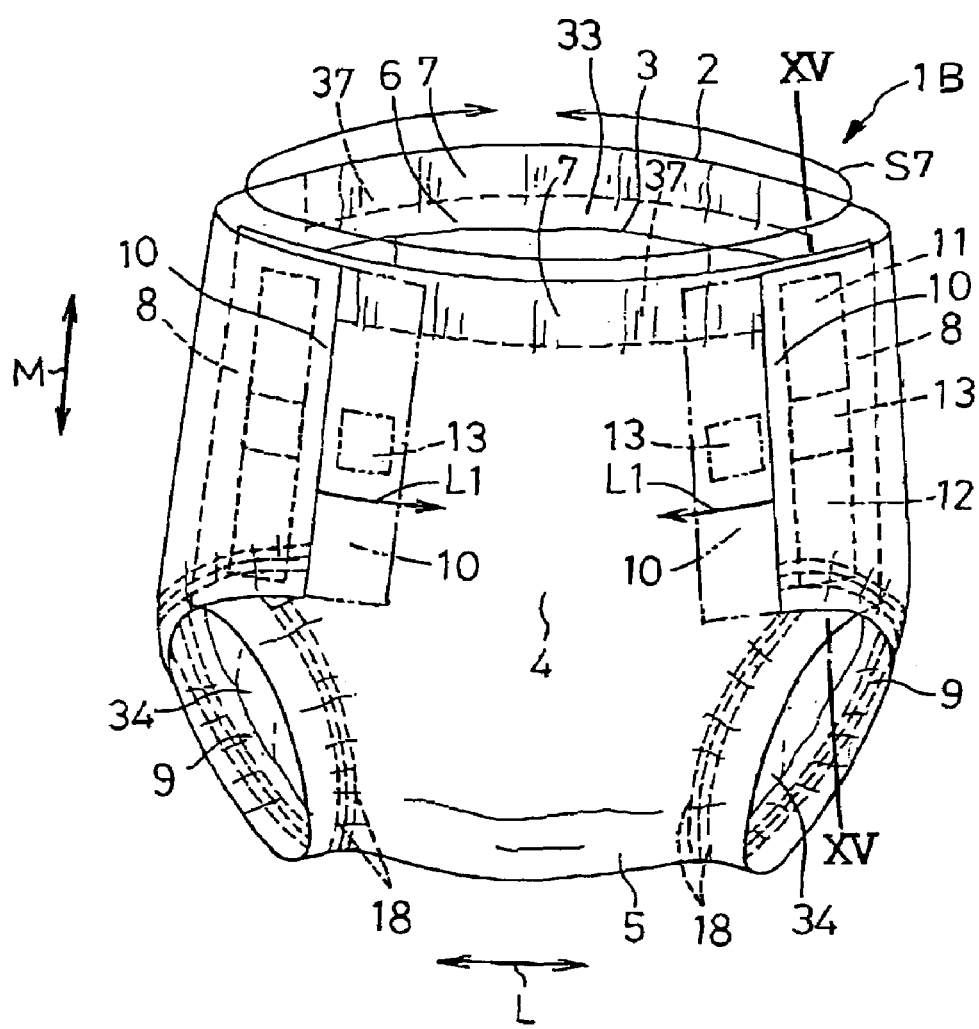
FIG. 14 is a perspective view showing the article of FIG. 9 as put on the wearer's body.
Figure 15:
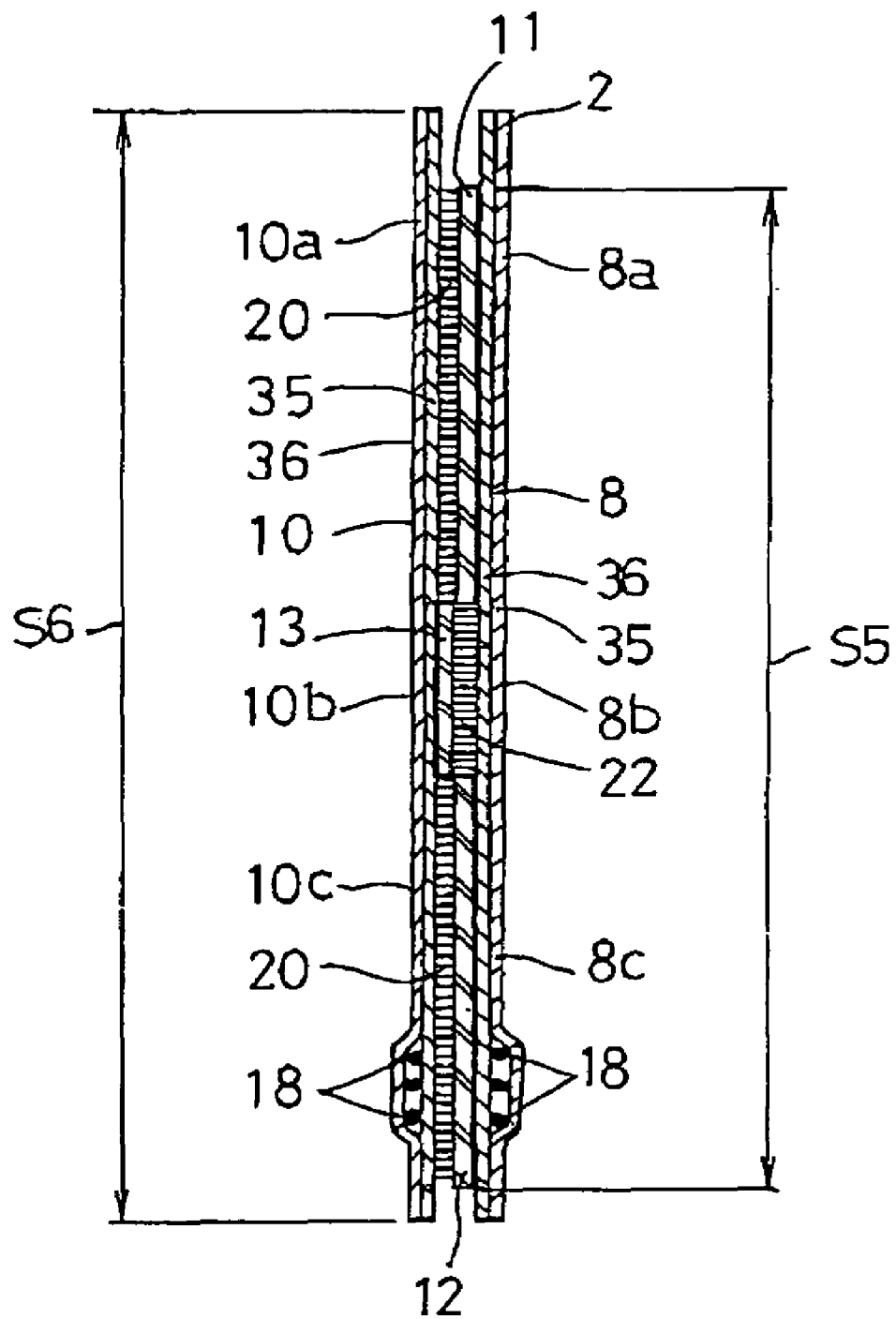
FIG. 15 is a sectional view taken along the line XV-XV in FIG. 14.

FIG. 14 is a perspective view showing the article 1B of FIG. 9 as put on the wearer's body and FIG. 15, is a sectional view taken along a line XV-XV in FIG. 14. In FIG. 14, a transverse direction is indicated by an arrow L, a longitudinal direction is indicated by an arrow M and the side edge portions 10 of the rear waist region 6 having been moved toward a transversely middle zone of the front waist region 4 are indicated by chain double-dashed lines. A sequence for disposal of this article 1B is same as in the case of FIG. 1 and therefore repeated description of the sequence is eliminated here.

In the article 1B, the hooks 20 are caught by individual fibers of the nonwoven fabric layer 35 constituting the outer sheet 2 and thereby the first and second engagement members 11, 12 are engaged with the inner surface of the side edge portions 10 of the rear waist region 6. Simultaneously, the hooks 22 are caught by individual fibers of the nonwoven fabric layer 36 constituting the outer sheet 2 and thereby the third engagement member 13 is engaged with the outer surface of the side edge portions 8 of the front waist region 8. In this way, the front and rear waist regions 4, 6 are connected with each other along the side edge portions 8, 10 thereof.

The third engagement members 13 are present neither in the longitudinally upper zone 10a nor in the longitudinally lower zone 10c of the respective side edge portions 10 of the rear waist region 6 and therefore there is no possibility that the third engagement members 13 might be exposed on the inner side of the article 1B even if the positions at which the side edge portions 8, 10 of the front and rear waist regions 4, 6 are connected together are shifted aside. In the article 1B, even if the longitudinally upper and lower zones 10a, 10c of the side edge portions 10 contact with the wearer's front waist and legs, there is no anxiety that the wearer's skin might experience any uncomfortable irritation. This is for the reason that none of the hooks 22 are present in these zones 10a, 10c and merely the zones of the outer sheet 2 contact with the wearer's front waist and legs. In the article 1B, the length dimension S4 of the third engagement member 13 is smaller than those of the first and second engagement members 11, 12 and therefore the article 1B can more reliably prevent the third engagement members 13 from coming in contact with the wearer's skin than the article 1A ensures it.

When the article 1B is put on the wearer's body and the first, second and third engagement members 11, 12, 13 are almost linearly aligned one with another in the longitudinal direction, each column defined by the first, second and third engagement members 11, 12, 13 includes none of blank zones between the first and second engagement members 11, 13 linearly aligned with each other in the longitudinal direction as well as between the second and third engagement members 12, 13 linearly aligned with each other in the longitudinal direction, as will be apparently understood from FIGS. 14 and 15. Compared to the case in which the column defined by these engagement members 11, 12, 13 includes one or more blank zones, the side edge portions 8, 10 of the front and rear waist regions 4, 6 can be further more reliably connected together.

A total length dimension S5 of these engagement members 11, 12, 13 measured in the longitudinal direction substantially corresponds to a length dimension S6 of the side edge portions 8, 10 of the front and rear waist regions 4, 6. With such dimensioning, the side edge portions 8, 10 of the front and rear waist regions 4, 6 are engaged with one another over a generally full range of the length dimension S6 as the first, second and third engagement members 11, 12, 13 are engaged with the outer surface of the front waist region 4 and the inner surface of the rear waist regions 6, respectively. Thus these side edge portions 8, 10 of the front and rear waist regions 4, 6 can be reliably engaged with one another.

With the article 1B put on the wearer's body, the side edge portions 8, 10 of the front and rear waist regions 4, 6 may be disconnected one from another on the wearer's body, the side edge portions 10 of the rear waist region 6 may be pulled toward the transversely intermediate zone of the front waist region 4 as indicated by the arrow L1, then, the respective inner surfaces of the side edge portions 10 of the rear waist region 6 may be placed upon the outer surface of the front waist region 4 at desired positions to connect again the front and rear waist regions 4, 6 with each other by means of these first, second and third engagement members 11, 12, 13.

After the article 1B has been put on the wearer's body, the front and rear waist regions 4, 6 can be connected again with each other by means of the engagement members 11, 12, 13 as indicated by chain double-dashed lines. In this way, the side edge portions 10 of the rear waist region 6 may be connected with the side edge portions 8 of the front waist region 4 at the appropriate positions to ensure that a dimension S7 of the article 1B in the waist surrounding direction is adjusted in conformity with the individual wearer's waist size without an anxiety that the article 1B might slip down along the wearer's waist during use of the article 1B.

The used article 1B may be prepared for disposal in a manner as will be described hereunder. Parent or care personnel may fold the crotch region 5 onto the outer surface of the front waist region 4, then draw the side edge portions 10 of the rear waist region 6 toward a transversely intermediate zone of the crotch region 5 and press the side edge portions 10 of the rear waist region 6 against the outer surface of the crotch region 5. By pressing the side edge portions 10 against the crotch region 5, the hooks 22 are caught by the individual fibers of the nonwoven fabric layer 36 constituting the outer sheet 2 and thereby the side edge portions 10 of the rear waist region 8 can be fastened to the outer surface of the crotch region 5 by means of the third engagement members 13.

Similarly to the case shown in FIG. 8, the used article 1B also can be maintained in its folded state by the third engagement members 13 serving to connect the side edge portions 10 of the rear waist region 6 to the outer surface of the crotch region 5 and therefore can be ready for disposal. More specifically, the waist-hole 33 as well as the leg-holes 34 of the used article 1B are maintained in closed state and therefore it is not apprehended that body waste or odor thereof might leak out from the article 1B through the waist-hole 33 and/or the leg-holes 34.

It is unnecessary for the article 1B to fold the side edge portions 10 of the rear waist region 6 toward the inner side of the article 1B for disposal, because the third engagement members 13 face the outer surface of the crotch region 5. Merely by pressing the side edge portions 10 against the outer surface of the crotch region 5, the article 1B can be effectively folded for disposal. In the article 1B folded in this manner, a shearing force is exerted on the side edge portions 10 of the rear waist region 6 as well as on the outer surface of the crotch region 5 and rather enhances engagement of the third engagement members 13 with the outer surface of the crotch region 5. In this way, there is no anxiety that the article 1B might be unintentionally unfolded.

Material for the topsheet 23 is not limited to the hydrophilic fibrous nonwoven fabric and it is possible to form the topsheet 21 from a hydrophobic fibrous nonwoven fabric having a plurality of apertures. It is possible to use a breathable liquid-impervious plastic film as material for the backsheet 22. The outer sheet 2, the backsheet 24 and the leak-barrier sheets 28 may be formed also from a composite nonwoven fabric (SM nonwoven fabric or SMS nonwoven fabric) composed of a melt blown fibrous nonwoven fabric having a high water-resistance and a spun bond fibrous nonwoven fabric being high in strength as well as in flexibility laminated on at least one side of the melt blown fibrous nonwoven fabric.

Materials for the fibrous nonwoven fabric layers may be selected from the group consisting of spun lace-, needle punch-, melt blown-, thermal bond-, spun bond- and chemical bond-nonwoven fabric layers. Material for the hydrophilic fibrous nonwoven fabric may be selected from the group consisting of synthetic fibers modified to be hydrophilic, semi-synthetic fibers, regenerated fibers and mixture thereof. The hydrophobic fibrous nonwoven fabric may contain water-repellent finished semi-synthetic fibers or regenerated fibers. Although not specified, the synthetic fibers may be selected from the group consisting of polyester-, polyacrylonitril-, polyvinyl chloride-, polyethylene-, polypropylene- and polystyrene-based synthetic fibers. It is also possible to use the synthetic fiber selected from the group consisting of core-sheath conjugate fibers, side-by-side conjugate fibers, modified macaroni fibers, microporous fibers and fused type conjugate fibers.

The stretchable fibrous nonwoven fabric layers 35, 36 constituting the outer sheet 2 of FIG. 9 may be formed from a melt blown nonwoven fabric or spun bond nonwoven fabric. It is possible to use, as component fibers of the stretchable nonwoven fabric layers 35, 36, stretchable fibers melt spun from thermoplastic elastomer resin. It is also possible to form the outer sheet 2 from a composite nonwoven fabric composed of a stretchable hydrophobic fibrous nonwoven fabric made of thermoplastic elastomer resin fibers and a hydrophobic fibrous nonwoven fabric made of crimped fibers melt spun from thermoplastic synthetic resin selected from the group consisting of polypropylene, polyethylene and polyester laminated on at least one surface of the aforementioned hydrophobic fibrous nonwoven fabric.

Permanently bonding of the sheets 2, 23, 24, 28 to one another, permanently bonding of the core 25 to the sheets 23, 24 and permanently bonding of the elastic members 16, 17, 18, 32 to the sheets 2, 28 may be achieved by use of adhesives. It is preferred to coat the outer sheet 2, the top- and backsheets 23, 24 and the leak-barrier sheets 28 with the adhesive in a pattern selected from the group consisting of a spiral pattern, wave-pattern, zigzag pattern, dotted pattern and stripe-pattern. By coating the outer sheet 2, the top- and backsheets 23, 24 and the leak-barrier sheets 28 with the adhesive in such pattern, these sheets 2, 23, 24, 28 can be intermittently and permanently bonded one to another, the core 25 can be intermittently and permanently bonded to the sheets 23, 24 and the elastic members 16, 17, 18, 32 can be intermittently and permanently bonded to the sheets 2, 28. The outer sheet 2 may be permanently bonded to the engagement members 11, 12, 13 by use of adhesive or welding technique such as sonic sealing or heat sealing. The adhesive may be selected from a group consisting of hot melt adhesive, acrylic adhesive and rubber adhesive.

When the engagement members 11, 12, 13 are permanently bonded to the outer sheet 2 using adhesive, a content of finish surface active agent in the nonwoven fabric layers 14, 15, 35, 36 constituting the outer sheet 2 is preferably 0.04 wt per total weight of these nonwoven fabric layers 14, 15, 35, 36 as measured by solvent extraction method (prescribed by JIS L 1015 7.22). If the content of the finish surface active agent exceeds 0.04 wt, the finish surface active agent will progressively deteriorate an adhesive force of the adhesive as the time elapses and an adhesive strength of the engagement members 11, 12, 13 to the outer sheet 2 will be correspondingly deteriorated until the engagement members 11, 12, 13 may be peeled off from the outer sheet 2. So far as the content of the finish surface active agent is less than 0.04 wt, the adhesive is reliably protected against deterioration of its adhesive force and, even if the articles 1A, 1B are stored for long period, the adhesive strength of the engagement members 11, 12, 13 to the outer sheet 2 is protected from deterioration. The finish surface active agent may be selected from a group consisting of anionic, nonionic, cationic, amphoteric surface active agents and mixtures thereof. Anionic or nonionic surface active agent may contain, if necessary to enhance adherence to the fiber, fatty wax, fatty acid, higher alcohol, mineral oil or hardened oil.

What is claimed is:

1. A disposable wearing article, comprising:
   front and rear waist regions,
   a crotch region extending in a longitudinal direction of the article between the front and rear waist regions, and
   paired engagement members positioned along transversely opposite side edges of said front and rear waist regions so that said front and rear waist regions are connectable together by means of said engagement members, said engagement members comprising:
       first and second hook members permanently attached to an outer surface of said front waist region along the transversely opposite side edge portions thereof, respectively, said first and second hook members being releasably engageable with an inner surface of said rear waist region, and
       third hook members permanently attached to the inner surface of said rear waist region along the transversely opposite side edge portions thereof, respectively, and wherein said first and second hook members are entirely spaced in the longitudinal direction of the article by a given dimension selected to permit the third hook member to releasably engage the outer surface of said front waist region between the first and second hook members when the front and rear waist regions are connected together by means of said engagement members.

2. The article according to claim 1, wherein a length dimension of said third hook members measured in the longitudinal direction substantially corresponds to or is slightly larger than the dimension by which said first and second hook members are spaced from one another in the longitudinal direction.

3. The article according to claim 1, wherein the outer surface of the front waist region and the inner surface of the rear waist region are formed essentially of the same material engageable with said first through third hook members.

4. The article according to claim 1, wherein the outer surface of the front waist region and the inner surface of the rear waist region are formed of the same type of material.

5. The article according to claim 1, wherein an outer surface of the crotch region is formed, at least in part, of the same fabric as the outer surface of the front waist region is formed, thereby allowing the third hook members to releasably engage the outer surface of the crotch region to hold the article in a rolled configuration after use.

6. The article according to claim 1, wherein the third hook members are located so that when the rear waist region is overlaid on the front waist region the first, second and third hook members assume an essentially aligned configuration without overlapping one another.

7. The article according to claim 6, wherein a total length dimension of said first, second and third hook members measured in the longitudinal direction when said first through third hook members are aligned one with another in the longitudinal direction substantially corresponds to a length dimension of said transversely opposite side edge portions in said front and rear waist regions measured in the longitudinal directions.

8. The article according to claim 1, wherein
   the inner surface of the rear waist region is adapted to face a wearer's body, in use;
   the outer surface of the front waist region is adapted to face away from the wearer's body, in use; and
   the inner surface of the rear waist region and the outer surface of the front waist region are adapted to face each other when the rear waist region is overlaid on the front waist region, in use, with the first and second hook members releasably engaging the inner surface of the rear waist region at locations above and below said third hook member while the third hook member releasably engaging the outer surface of the front waist region between the first and second hook members.

9. The article according to claim 8, wherein a length dimension of said third hook members measured in the longitudinal direction is smaller than a length dimension of said first and second hook members measured in the longitudinal direction.

10. The article according to claim 8, wherein
    said first through third hook members have substantially the same width as measured in a transverse direction perpendicular to the longitudinal direction of the article; and
    the width of each of said first through third hook members is substantially constant throughout a length of said hook member as measured in the longitudinal direction.

11. The article according to claim 10, wherein the length of said third hook members is substantially the same as the dimension by which said first and second hook members are spaced from one another in the longitudinal direction.

12. The article according to claim 10, wherein the length of said third hook members is greater than the dimension by which said first and second hook members are spaced from one another in the longitudinal direction.

13. The article according to claim 10, wherein the length of said third hook members is smaller than the length of each of said first and second hook members.

14. The article according to claim 10, wherein an entire area of the outer surface of the front waist region that is located between the first and second hook members and has substantially the same width as said first and second hook members is releasably engageable with the third hook members.

15. The article according to claim 8, wherein said first and second hook members are entirely spaced in the longitudinal direction by an area of the outer surface of the front waist region that is located between the first and second hook members, and an entirety of said area is releasably engageable with the third hook members.

16. A disposable wearing article, comprising:
    front and rear waist regions,
    a crotch region extending in a longitudinal direction of the article between the front and rear waist regions, and
    paired engagement members positioned along transversely opposite side edges of said front and rear waist regions so that said front and rear waist regions are connectable together by means of said engagement members, said engagement members comprising:
        first and second engagement members permanently attached to one of (a) an outer surface of said front waist region and (b) inner surface of said rear waist region, along the transversely opposite side edge portions thereof, respectively, said first and second engagement members being releasably engageable with the other of the outer surface of said front waist region and the inner surface of said rear waist region, and
        third engagement members permanently attached to the other of the outer surface of said front waist region and the inner surface of said rear waist region along the transversely opposite side edge portions thereof, respectively, and wherein the inner surface of the rear waist region is adapted to face a wearer's body, in use;

the outer surface of the front waist region is adapted to face away from the wearer's body, in use;

the inner surface of the rear waist region and the outer surface of the front waist region are adapted to face each other when the rear waist region is connected to while being overlaid on the front waist region, in use, with the first and second engagement members releasably engaging the other of the outer surface of said front waist region and the inner surface of said rear waist region at locations above and below said third engagement member, while the third engagement member releasably engaging said one of the outer surface of said front waist region and the inner surface of said rear waist region between the first and second engagement members;

said first and second engagement members are entirely spaced in the longitudinal direction by an area of said one of the outer surface of said front waist region and the inner surface of said rear waist region that is located between the first and second hook members, and an entirety of said area is releasably engageable with the third engaging members; and all said first though third engagement members are hook members.

* * * * *

UNITED STATES PATENT AND TRADEMARK OFFICE
CERTIFICATE OF CORRECTION

PATENT NO.         : 7,404,812 B2
APPLICATION NO. : 10/920350
DATED              : July 29, 2008
INVENTOR(S)        : Toshifumi Otsubo et al.

It is certified that error appears in the above-identified patent and that said Letters Patent is hereby corrected as shown below:

On the title page item [75], the second inventor's name should read as follows:

(75) Inventors: Toshifumi OTSUBO, Kagawa-ken (JP);

Tomoko SUGITO, Kagawa-ken (JP)

Signed and Sealed this

Seventh Day of October, 2008

JON W. DUDAS
*Director of the United States Patent and Trademark Office*